US006255316B1

(12) United States Patent
Marti et al.

(10) Patent No.: US 6,255,316 B1
(45) Date of Patent: Jul. 3, 2001

(54) DICYCLANIL POLYMORPHS AND HYDRATES AND THEIR PREPARATION

(75) Inventors: Erwin Marti, Basel; Walter Oechslein, Kaiseraugst, both of (CH); André Joseph Geoffroy, Habsheim (FR)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 09/486,105

(22) PCT Filed: Aug. 25, 1998

(86) PCT No.: PCT/EP98/05387

§ 371 Date: Feb. 22, 2000

§ 102(e) Date: Feb. 22, 2000

(87) PCT Pub. No.: WO99/10333

PCT Pub. Date: Mar. 4, 1999

(30) Foreign Application Priority Data

Aug. 27, 1997 (CH) .................................. 1998/97

(51) Int. Cl.$^7$ ........................ A61K 31/505; C07D 239/50
(52) U.S. Cl. ............................................. 514/275; 544/323
(58) Field of Search .............................. 544/323; 514/275

(56) References Cited

U.S. PATENT DOCUMENTS 4,783,468  11/1988  Kristinsson et al. .................. 514/275

FOREIGN PATENT DOCUMENTS 0 244 360    11/1987  (EP) .
95 03282  *  2/1995   (WO) .

* cited by examiner

Primary Examiner—Richard L. Raymond
Assistant Examiner—Venkataraman Balasubramanian
(74) Attorney, Agent, or Firm—Michael U. Lee

(57) ABSTRACT

The present invention relates to several new, polymorphous crystal forms of Dicyclanil, and hydrates and solvates thereof, as well as the preparation thereof. In particular, the invention relates to substantially pure crystal forms of Dicyclanil, having characteristic lattice structures, which are effective for the control of insects and ectoparasites.

19 Claims, No Drawings

DICYCLANIL POLYMORPHS AND HYDRATES AND THEIR PREPARATION

The present invention relates to several new, polymorphous crystal forms of dicyclanil, the hydrates and solvates thereof, as well as the preparation thereof.

Dicyclanil is used as a veterinary drug for the control of ectoparasites on domestic and farm animals.

The morphology and polymorphology of organo-chemical active substances is of great importance to the chemical and pharmaceutical development thereof. Substances are known which only appear in a single crystal form; in addition, however, there are also substances which can form two, three or even more polymorphous crystal modifications. It is just as difficult to calculate or predict this possible morphological and structural variety and the respective physico-chemical, especially thermodynamic stability respect thereof on a scientific-mathematical basis, as it is to calculate or predict their different behaviour when they are administered to a living organism. The relevant polymorphism of an organo-chemical substance is always unpredictable in respect of the number of crystal modifications, the stability thereof and their behaviour in a living organism.

If two, three or more crystal modifications of a substance are known, then in general their absolute and relative physico-chemical stabilities may be determined. The unstable crystal modification or unstable crystal modifications normally signify instead a disadvantage through the entire chemical and pharmaceutical preparation process, since in each step of the process or in each intermediate storage, a partial or total conversion to the more stable modification may take place. Due to their meta-stability, many unstable crystal modifications may be maintained for lengthy periods. However, they may also transform spontaneously into a more stable modification at an indeterminate point in time. Such transformation processes cannot be foreseen and each substance behaves in a different way in this respect. The different crystal modifications of one and the same substance may differ considerably from one another in many respects. These differences in morphology and polymorphism may have drastic effects on the development, transport stability and storage stability of individual administration forms, on the ability to produce different administration forms, on their application, on the solubility in polar or non-polar, protic or aprotic solvents, on solubility in blood serum, and finally on bio-availability.

The same also applies in respect of the physical and chemical properties of dicyclanil, a compound of formula

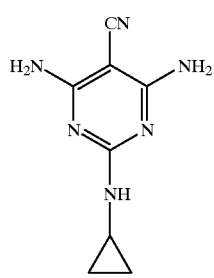

(I)

(2-cyclopropylamino-4,6-diaminopyrimidine-5-carbonitrile)

with a published melting point of 249–251°, which is disclosed in European Patent Specification EP-0 244 360 B1 both as a new compound and as an agent for the control of insects pests and ectoparasites on warm-blooded animals. Dicyclanil is effective as a growth regulator for insects and has special activity against Diptera species. Dicyclanil provides long-term protection of sheep against the widespread myasis flies such as *Lucilia sericata, Lucilia cuprina* and the like.

Application is preferably effected by means of the "pour-on" process, whereby the formulation is finely dispersed to the back of the sheep either directly or by a spray appliance. This type of application has considerable advantages, since only the exposed places are sprayed and effects on the environment are thus minimised.

It is precisely with formulations having suspended active substance, such as in the "pour-on" processes, that the different properties of the crystal modifications play a decisive role.

One crystal modification of dicyclanil is already known. Thus, the crystal form described in the above-mentioned publication is referred to hereinafter as modification A. Surprisingly, it has now been found that dicyclanil can occur in at least seven further, differing crystal modifications, hereinafter referred to as modifications B, C, D, E, F, G and H, whereby modification C has proved to be the crystalline dicyclanil hydrate and modification H the dicyclanil-propanediol solvate, which possess unforeseen, advantageous properties over the previously known crystal form. All eight forms are significantly distinct from one another in respect of their physico-chemical properties, their stability and, in part, their biological behaviour. The present invention relates primarily to the crystal modification D of dicyclanil, which is stable in non-polar and in mixtures of non-polar and polar dispersing agents, and is insignificantly soluble in these dispersing agents, and it relates to the production thereof.

In DSC (Differential Scanning Calorimetry), this new crystal modification D of dicyclanil shows a transformation in the temperature range of between 150° C. and 166° C. at a heating rate of 10° C./min. The temperature range and the kinetics of this conversion is dependent both on external measurement conditions and on different properties of the respective sample of dicyclanil. The preferred characterisation of crystal modification D of dicyclanil is effected by means of the interlattice plane distances d of an X-ray diffraction diagram:

d in [Å]: 11.4±0.2, 8.7±0.2, 7.1±0.2, 5.92±0.05, 5.75±0.05, 5.70±0.05, 4.45±0.05, 4.40±0.05, 4.15±0.05, 3.96±0.05, 3.94±0.05, 3.80±0.05, 3.78±0.05, 3.72±0.05, 3.53±0.05, 3.41±0.05, 3.32±0.05, 2.96±0.05, 2.92±0.05, 2.84±0.05 and 2.83±0.05.

The most intensive reflexes in the X-ray diffraction diagram thus give the following interlattice plane distances:

d in [Å]: 11.4±0.2, 8.7±0.2, 5.92±0.05, 5.75±0.05, 5.70±0.05, 4.15±0.05, 3.96±0.05, 3.80±0.05, 3.78±0.05 and 3.53±0.05.

The enthalpy change generally observed in the DSC for dicyclanil between 150° C. and 166° C. can be clearly explained by means of a heatable powder diffractometer using copper-Kα X-ray radiation. The crystal modification D, which is characterised by the above-indicated interlattice plane distances, is transformed at between 100° C. and 200° C. into another solid, which is expressed in a different set of interlattice plane distances.

This new specific crystal form D has superior properties over all other known crystal modifications of dicyclanil and its known hydrate. In particular, as a suspension in non-polar, or mixtures of non-polar and polar, dispersing agents, especially in mixtures of non-polar dispersing agents with water, the crystal modification D is physico-chemically and thermodynamically more stable than the other known modifications, including the hydrate, in the usual temperature range. For these reasons, crystal modification D is more suitable both for the development and production of the chemical substance in solid form and for the development and production of insecticide formulations or of preformulations thereof, and also in respect of the application thereof in the field. If all other known modifications of dicyclanil are suspended in non-polar or mixtures of non-polar and polar dispersing agents, a slow transformation of the modification, or of the hydrate or solvate, possibly also a spontaneous transformation, but generally an unpredictable transformation in terms of time and place, may take place, to form a more stable crystal modification. Transformations of solids of this kind are generally associated with a change in the crystal habit and with a change in size of the crystals. These changes lead to various, enormous defects, which, through sedimentation and/or separation of the suspension, end in formulations that can no longer be technically applied. In general, the insecticidal activity of such a formulation will no longer be detectable.

Crystal modification D is thermodynamically stable, but as indicated above, at a heating rate of 10° C./min. in a temperature range between 150° C. and 166° C., transforms into a crystal modification with a melting point range between 235 and 255° C. The melting point of the crystal modification formed lies at 247° C., conforming with the melting point of 249–251° C. of crystal modification A already described in patent application P 0244360 B1. This crystal form A in pure form has a melting point of 247–255° C.

Apart from these two crystal modifications A and D and other crystal modifications, as mentioned, a hydrate and a propanediolate of dicyclanil also exist.

Crystal modifications, hydrates and solvates may be distinguised by their X-ray powder diagrams. X-ray powder diagrams, taken with a Guinier camera in transmission geometry and using Cu-K$\alpha_1$ radiation, are preferably used to characterise solid forms of organic substances. In particular, X-ray diffraction diagrams are used advantageously and with good powers of affirmation to determine the different crystal modifications of a substance. In the case of hydrates and solvates, additional methods have to be used, such As thermogravimetry or thermogravimetry-Fourier-transform-infrared-spectroscopy (TG-FTIR) and other substance-specific methods.

To characterise the present crystal modifications D of dicyclanil according to the invention, measurements were carried out with a Guinier camera using samples of substance which were kept at room temperature.

The diagrams recorded on X-ray film were measured with a Line Scanner and the interlattice plane distances of the most important lines were calculated.

TABLE 1

X-ray diffraction diagram
(interlattice plane distances and
intensities of the most important lines)
of crystal modification D of dicyclanil.

| d [Å] | Intensity |
|---|---|
| 11.4 | very strong |
| 8.7 | very strong |
| 7.1 | weak |
| 5.92 | medium |
| 5.75 | medium |
| 5.70 | medium |
| 5.48 | very weak |
| 4.59 | very weak |
| 4.45 | weak |
| 4.40 | weak |
| 4.35 | very weak |
| 4.15 | strong |
| 4.10 | very weak |

TABLE 1-continued

X-ray diffraction diagram
(interlattice plane distances and
intensities of the most important lines)
of crystal modification D of dicyclanil.

| d [Å] | Intensity |
|---|---|
| 4.03 | very weak |
| 3.96 | medium |
| 3.94 | weak |
| 3.80 | strong |
| 3.78 | very strong |
| 3.72 | weak |
| 3.53 | strong |
| 3.41 | medium |
| 3.32 | weak |
| 3.23 | very weak |
| 3.14 | very weak |
| 3.11 | very weak |
| 3.08 | very weak |
| 2.96 | weak |
| 2.92 | weak |
| 2.84 | weak |
| 2.83 | weak |
| 2.73 | very weak |

For comparison, in the following Tables 2, 3, 4, 5 and 6, the X-ray diffraction diagrams of the above-described crystal modification A of dicyclanil are reproduced, as are those of the new crystal modifications B, E, F and G. In order to produce these, the respective crystal modification consisting of modification A produced above all by the process according to EP-B1-0,244,360, or consisting of the mixture of modifications A and B, is prepared by seeding with an appropriate amount of seeding nucleus of a corresponding modification. Each of the crystal modifications then requires, apart from an appropriate solvent, also certain temperature conditions and transformation times.

TABLE 2

X-ray diffraction diagram
(interlattice plane distances and
intensities of the most important lines)
of crystal modification A of dicyclanil.

| d [Å] | Intensity |
|---|---|
| 11.3 | very weak |
| 8.9 | very strong |
| 8.0 | strong |
| 7.5 | medium |
| 5.80 | medium |
| 5.72 | strong |
| 5.62 | weak |
| 5.13 | weak |
| 5.08 | very weak |
| 4.73 | weak |
| 4.45 | strong |
| 4.40 | very weak |
| 4.35 | very weak |
| 4.28 | very weak |
| 4.14 | medium |
| 4.06 | very weak |
| 4.01 | weak |
| 3.72 | medium |
| 3.39 | medium |
| 3.27 | weak |
| 3.19 | weak |
| 3.13 | weak |
| 3.05 | very weak |

TABLE 2-continued

X-ray diffraction diagram
(interlattice plane distances and
intensities of the most important lines)
of crystal modification A of dicyclanil.

| d [Å] | Intensity |
|---|---|
| 2.99 | weak |
| 2.96 | weak |
| 2.90 | weak |
| 2.86 | weak |
| 2.83 | weak |

TABLE 3

X-ray diffraction diagram
(interlattice plane distances and
intensities of the most important lines)
of crystal modification B of dicyclanil.

| d [Å] | Intensity |
|---|---|
| 9.2 | strong |
| 8.3 | strong |
| 5.89 | very strong |
| 4.59 | medium |
| 4.41 | medium |
| 3.68 | very strong |
| 3.36 | weak |
| 3.11 | very weak |
| 3.06 | weak |
| 3.00 | very weak |
| 2.97 | very weak |
| 2.92 | very weak |
| 2.82 | very weak |
| 2.68 | very weak |
| 2.64 | very weak |

TABLE 4

X-ray diffraction diagram
(interlattice plane distances and
intensities of the most important lines)
of crystal modification E of dicyclanil.

| d [Å] | Intensity |
|---|---|
| 9.5 | strong |
| 8.0 | strong |
| 7.6 | strong |
| 6.0 | very strong |
| 5.57 | weak |
| 5.47 | strong |
| 4.71 | strong |
| 4.38 | medium |
| 4.27 | medium |
| 4.18 | very strong |
| 4.12 | very weak |
| 3.99 | strong |
| 3.93 | weak |
| 3.74 | medium |
| 3.66 | medium |
| 3.61 | medium |
| 3.53 | strong |
| 3.42 | very weak |
| 3.37 | very strong |
| 3.21 | weak |
| 3.14 | medium |
| 3.08 | strong |
| 3.01 | very weak |
| 2.98 | weak |
| 2.88 | medium |
| 2.85 | very weak |
| 2.79 | weak |

TABLE 4-continued

X-ray diffraction diagram
(interlattice plane distances and
intensities of the most important lines)
of crystal modification E of dicyclanil.

| d [Å] | Intensity |
|---|---|
| 2.73 | weak |
| 2.66 | very weak |

TABLE 5

X-ray diffraction diagram
(interlattice plane distances and
intensities of the most important lines)
of crystal modification F of dicyclanil.

| d [Å] | Intensity |
|---|---|
| 11.3 | very weak |
| 9.3 | weak |
| 9.1 | weak |
| 8.9[1] | very weak |
| 8.6 | very weak |
| 8.4 | very strong |
| 8.0[1] | very weak |
| 7.9 | very weak |
| 7.5[1] | very weak |
| 6.9 | medium |
| 6.4 | weak |
| 5.91 | strong |
| 5.71[1] | weak |
| 5.67 | weak |
| 4.48 | medium |
| 4.44[1] | very weak |
| 4.37 | medium |
| 4.14[1] | very weak |
| 4.10 | weak |
| 3.99 | weak |
| 3.86 | very weak |
| 3.77 | very weak |
| 3.72[1] | medium |
| 3.52 | weak |
| 3.49 | weak |
| 3.39[1] | weak |
| 3.31 | very weak |
| 3.25 | very weak |
| 3.17 | very weak |
| 3.11 | very weak |
| 3.04 | weak |
| 2.96 | very weak |
| 2.90 | weak |
| 2.87 | very weak |
| 2.83 | very weak |
| 2.66 | very weak |
| 2.63 | very weak |

[1]interlattice plane distances of crystal modification A

TABLE 6

X-ray diffraction diagram
(interlattice plane distances and
intensities of the most important lines)
of crystal modification G of dicyclanil.

| d [Å] | Intensity |
|---|---|
| 9.0 | very strong |
| 8.3 | weak |
| 7.8 | strong |
| 5.92 | very strong |
| 5.59 | weak |
| 5.37 | very weak |
| 4.94 | weak |

TABLE 6-continued

X-ray diffraction diagram
(interlattice plane distances and
intensities of the most important lines)
of crystal modification G of dicyclanil.

| d [Å] | Intensity |
|---|---|
| 4.60 | very weak |
| 4.52 | strong |
| 4.43 | medium |
| 4.14 | very weak |
| 3.98 | very strong |
| 3.84 | very weak |
| 3.81 | very weak |
| 3.68 | weak |
| 3.63 | weak |
| 3.33 | medium |
| 3.08 | weak |
| 3.07 | weak |
| 3.01 | medium |
| 2.97 | very weak |
| 2.94 | very weak |
| 2.83 | weak |
| 2.69 | very weak |

The dihydrate of dicyclanil, with a water content of 15.3%, defined as crystal modification C, is formed from crystal modifications A or B, or from mixtures thereof, in water by seeding with modification C.

TABLE 7

X-ray diffraction diagram
(interlattice plane distances and
intensities of the most important lines)
of crystal form C (dihydrate with a water
content of 15.3%) of dicyclanil.

| d [Å] | Intensity |
|---|---|
| 8.9 | weak |
| 8.4 | very strong |
| 6.8 | strong |
| 6.3 | medium |
| 4.41 | strong |
| 4.32 | medium |
| 3.97 | medium |
| 3.70 | weak |
| 3.57 | medium |
| 3.48 | very weak |
| 3.43 | weak |
| 3.35 | medium |
| 3.19 | weak |
| 3.17 | very weak |
| 3.02 | medium |
| 3.01 | medium |
| 2.92 | strong |
| 2.87 | medium |
| 2.70 | weak |
| 2.66 | very weak |
| 2.64 | weak |
| 2.48 | very weak |
| 2.34 | weak |
| 2.32 | weak |
| 2.23 | very weak |
| 2.16 | weak |
| 2.14 | weak |
| 2.02 | weak |
| 1.88 | weak |
| 1.85 | weak |

The dicyclanil-propanediol solvate of dicyclanil, defined as crystal modification H, is formed from crystal modifications A or B, or from mixtures thereof, in propanediol by seeding with modification H.

TABLE 8

X-ray diffraction diagram
(interlattice plane distances and
intensities of the most important lines)
of crystal modification H
(dicyclanil-propanediol solvate) of dicyclanil.

| d [Å] | Intensity |
|---|---|
| 11.2 | very weak |
| 9.4 | medium |
| 8.4 | very strong |
| 7.0 | strong |
| 6.4 | medium |
| 5.71 | medium |
| 5.58 | very weak |
| 4.69 | very weak |
| 4.49 | strong |
| 4.36 | strong |
| 4.13 | very strong |
| 4.0 | very weak |
| 3.89 | strong |
| 3.75 | very strong |
| 3.70 | very weak |
| 3.62 | very weak |
| 3.54 | strong |
| 3.50 | strong |
| 3.26 | weak |
| 3.17 | weak |
| 3.12 | weak |
| 3.05 | medium |
| 2.97 | very weak |
| 2.94 | very weak |
| 2.90 | weak |
| 2.88 | very weak |
| 2.84 | very weak |
| 2.79 | weak |
| 2.73 | very weak |
| 2.66 | weak |
| 2.63 | weak |

In addition, the present invention relates to a process for the production of the crystal modification D of dicyclanil according to the invention.

This process is characterised in that, in at least one process step, a suspension of dicyclanil of known or unknown or unspecified morphological composition with a grain size distribution of 0.4 to 6 μm is maintained at elevated temperature in a solvent or in a mixture of solvents of suitable polarity.

Polar solvents are for example polar organic compounds such as low alcohols, low ketones, low nitriles and low cyclic ethers, or water or mixtures thereof. The term "low" indicates organic compounds which contain 1 to 8 carbon atoms and one or two hetero atoms such as oxygen, nitrogen and/or sulphur. Preferred polar organic solvents are water-miscible organic solvents, such as methanol, ethanol, n-propanol, isopropanol, n-butanol, t-butanol, octanol, 1,2-propanediol, acetone, ethyl methyl ketone, acetonitrile, tetrahydrofuran or dioxane. Especially advantageous for the production of the crystal modification D of dicyclanil according to the invention are lower alcohols or mixtures thereof with water, especially 1-octanol and 1,2-propanediol or mixtures thereof with water. 1-octanol and 1,2-propanediol are most particularly preferred.

Elevated temperature indicates the temperature range from room temperature to boiling point of the solvent or solvent mixture, whereby the temperature range of about 30° C. to 60° C., especially from about 35° C. to 50° C., is preferred.

In a preferred embodiment of the process, at least one seeding crystal of crystal modification D of dicyclanil is added. Suitable seeding crystals of crystal modification D of dicyclanil may be produced for example in situ from a less stable solid, e.g. from a less stable crystal modification or from a mixture of less stable crystal modifications by tempering a suspension at elevated temperature for an appropriate length of time.

In a further embodiment, crystal modification D is formed during the preparation process of a formulation. In this, several part volumes of differing composition are produced under suitable conditions, and are subsequently combined in partial steps, so that an aqueous suspension-emulsion is formed. These part volumes consist firstly essentially of an emulsifier which is homogeneously dispersed in water, secondly of an organic solvent, thirdly of an oil phase which contains a stabiliser, fourthly of dicyclanil suspended in water, comprising one of the less stable crystal modifications or a mixture of the less stable crystal modifications. A surface-active substance is added to this fourth part volume in order to improve moistening of the crystals. To the first part volume, the other part volumes are added in succession under intense homogenisation. At the end, the formulation is set to the neutral pH value using a lye, and is brought to the desired volume with water. This formulation has substantial advantages, such as high concentration of dicyclanil, low viscosity—which brings with it good dispersement and good spray behaviour—good galenic, chemical and physico-chemical stability, especially thermodynamic stability, as a result of the dicyclanil which is suspended in the form of crystal modification D.

Depending on the type of active ingredient to be formulated, the surface-active compounds may be non-ionic, cationic and/or anionic surfactants or surfactant mixtures having good emulsifying, dispersing and wetting properties. The surfactants listed below should only be regarded as examples; in literature appertaining to this, many further surfactants are described, which are customary in formulation techniques and are suitable according to the invention.

The non-ionic surfactants are primarily polyglycol ether derivatives of aliphatic or cyclo-aliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical or the alkylphenols. Also suitable are water-soluble polyethylene oxide adducts to polypropylene glycol, ethylene diamino polypropylene glycol and alkyl polypropylene glycol, containing 20 to 250 ethylene glycol ether groups and 10 to 100 propylene glycol ether groups, and with 1 to 10 carbon atoms in the alkyl chain. The said compounds normally contain 1 to 5 ethylene glycol units per propylene glycol unit. Examples that may be mentioned are nonylphenol polyethoxyethanols, castor oil polyglycol ether, polypropylene-polyethylene oxide adducts, tributylphenoxy polyethoxyethanol, polyethylene glycol and octylphenoxy polyethoxyethanol. Furthermore, fatty acid esters of polyoxyethylene sorbitan may also be considered, such as polyoxyethylene sorbitan trioleate.

The cationic surfactants are in particular quaternary ammonium salts which have as substituents at least one alkyl radical with 8 to 22 C-atoms and as further substituents low, optionally halogenated alkyl, benzyl radicals or low hydroxyalkyl radicals. The salts preferably exist as halides, methyl sulphates or ethyl sulphates. Examples are stearyl trimethylammonium chloride and benzyl-di-(2-chloroethyl)-ethylammonium bromide.

Suitable anionic surfactants may be both water-soluble soaps and water-soluble synthetic, surface-active compounds. Suitable soaps are the alkali, alkaline earth and optionally substituted ammonium salts of higher fatty acids ($C_{10}$–$C_{22}$), such as the sodium or potassium salts of oleic or stearic acid, or of natural fatty acid mixtures, which may be obtained for example from coconut oil or tall oil; furthermore, the fatty acid methyl-taurine salts may also be mentioned. More frequently, however, synthetic surfactants are used, especially fat sulphonates, fat sulphates, sulphonated benzimidazole derivatives or alkylaryl sulphonates. As a rule, the fat sulphonates and sulphates exist as alkali, alkaline earth or optionally substituted ammonium salts, and generally have an alkyl radical with 8 to 22 C-atoms, alkyl also including the alkyl moiety of acyl radicals; examples which may be mentioned are the sodium or calcium salt of ligninsulphonic acid, of dodecyl-sulphuric acid ester or of a fat alcohol sulphate mixture produced from natural fatty acids. These also include the salts of sulphuric acid esters and sulphonic acids of fat alcohol/ethylene oxide adducts. The sulphonated benzimidazole derivatives preferably contain 2 sulphonic acid groups and a fatty acid radical with approximately 8 to 22 C-atoms. Alkylarylsulphonates are for example the sodium, calcium or triethanolammonium salts of dodecylbenzenesulphonic acid, or of dibutylnaphthalene-sulphonic acid or of a naphthalenesulphonic acid-formaldehyde condensation product. Furthermore, appropriate phosphates, such as salts of the phosphoric acid ester of a p-nonylphenol-(4-14)-ethylene oxide adduct or phospholipids may also be considered.

Suitable stabilisers are e.g. sodium benzoate, methyl-p-hydroxybenzoate, cetyl-trimethyl-ammonium-bromide, citric acid, tartaric acid, sorbic acid, phenols, alkylphenols, chlorinated phenols or optionally epoxidised vegetable oils, such as epoxidised coconut oil, rape-seed oil or soybean oil.

The following examples serve to illustrate the invention. They do not restrict the invention. Temperatures are given in degrees Celsius.

EXAMPLE 1
Production of Seeding Crystals of Crystal Modification D

For the in situ production of seeding crystals, 910 mg of dicyclanil, consisting of crystal modification A suspended in 4.93 g of 1-octanol, are brought to 50.0° C. in a water bath and stirred for ca. 24 hours. The suspension is subsequently filtered through a suction filter. The solid residue from the filter is dried at room temperature under a stream of protective gas, preferably nitrogen. The seeding crystals obtained are tested for chemical purity and morphological uniformity, and if no pure form of crystal modification D is present, the above process is repeated.

EXAMPLE 2
Production of Crystal Modification D 980 mg of dicyclanil of crystal modification A are suspended in 5.14 g of 1-octanol, then seeded with 100 mg of crystal modification D of dicyclanil. The suspension is maintained isothermally at 50° C. in a water bath whilst stirring. After ca. 24 hours, the suspension is filtered through a suction filter. The solid residue from the filter is dried at room temperature under a stream of nitrogen.

EXAMPLE 3
Production and Formulation of Crystal modification D

First of all, the following five part solutions are prepared:
Part Solution 1:
  12.0 g of Pemulen TR-2 (copolymer of acrylic acid with small portions of long-chained alkylacrylate comonomers, crosslinked with allyl pentaerythritol) are introduced into 1188 g of demineralised water whilst stirring vigorously at room temperature.
Part Solution 2:
  22.5 g of 4-hydroxybenzoic acid methyl ester and 45.0 g of 4-hydroxybenzoic acid propyl ester are dissolved in 3000 g of 1,2-propanediol whilst stirring at room temperature.
Part Solution 3:
  7,5 g of 2,6-di(t-butyl)-4-methylphenol are dissolved in 1500 g of medium-chained triglyceride (Miglyol 812) whilst stirring at room temperature. After this has dissolved completely, 300 g of distilled glyceryl monolinoleate (Myverol 18-92), which has already been melted at 40° C., are added and stirred until homogeneous.

Part Solution 4:

759.1 g of dicyclanil (technical, 98.8%) are suspended whilst stirring, at room temperature, in 2203 g of demineralised water, to which 37.5 g of polyoxyethylene sorbitan monolaurate (Tween 20) has already been added in order to improve wetting.

Part Solution 5:

7.5 g of EDTA disodium salt dihydrate and 0.3 g of food colouring E 124 (7-hydroxy-8-(4-sulphonato-1-naphthylazo)naphthalene-1,3-disulphonic acid, trisodium salt) are dissolved in 599.7 g of demineralised water whilst stirring, at room temperature.

To produce the formulation, part solution 1 is prepared, and mixed with 4000 g of water. Under intense homogenisation, part solutions 2, 3, 4 and 5 are added in succession. Afterwards, a pH of 7.0 is set with 1 N NaOH, and the formulation is made up to 15 l with water and subsequently stirred for ca. 30 minutes.

EXAMPLE 4
Production and Formulation of Crystal Modification D

First of all, the following three part solutions are prepared:

Part Solution 1:

0.78 kg of hydroxybenzoic acid methyl ester are dissolved whilst stirring, at room temperature, in 83.2 kg of 1,2-propanediol. Afterwards, 20.8 kg of demineralised water are added, and 0.42 kg of Pemulen TR-2 are dispersed in the resultant mixture whilst stirring vigorously.

Part Solution 2:

0.26 kg of 2,6-di(tert.-butyl)-4-methylphenol and 1.56 kg of hydroxybenzoic acid propyl ester are dissolved whilst stirring, at room temperature, in 52.0 kg of medium-chained triglyceride (Miglyol 812). After this has dissolved completely, 10.4 kg of distilled glyceryl monolinoleate (Myverol 18-92), which has already been melted at 40° C., are added and stirred until homogeneous.

Part Solution 3:

20.8 kg of 1,2-propanediol and 1.3 kg of polyoxyethylene sorbitan monolaurate (Tween 20) are added whilst stirring to 57.2 kg of demineralised water. Whist stirring, 26.5 kg of dicyclanil (technical, 99.2%) are suspended in this mixture, and also 0.26 kg of EDTA disodium salt dihydrate and 0.026 kg of food colouring E 124 are dissolved therein.

To produce the formulation, 130 kg of demineralised water are placed in an agitating kettle, and part solutions 1, 2 and 3 are added in succession with vigorous stirring. The resultant mixture is set at pH 7.0 with 4.35 kg of 1 N NaOH, and made up to 520 l with water.

EXAMPLE 5
Production of Crystal Form C (Dihydrate of Dicyclanil)

890 mg dicyclanil of crystal modification A are suspended in 4.6 g of distilled water and stirred at 40° C. for 24 hours and then filtered. The content of hydrate water, measured by means of thermogravimetry and DSC, is 15.3%, corresponding to a dihydrate having the crystal form C, characterized by means of an X-ray diffraction diagram.

EXAMPLE 6
Production of Crystal Modification B

In a stream of dry nitrogen 720 mg dicyclanil of crystal modification C are dried at 25° C. for 6 hours. The dry final product is characterized by means of an X-ray diffraction diagram as crystal modification B of dicyclanil.

EXAMPLE 7
Production of Crystal Modification F

To a solution of 1330 mg water and 23 mg polyoxyethylene sorbitan monolaurate (Tween 20) 456 mg dicyclanil are introduced whilst stirring at room temperature. The spontaneously formed suspension is stirred for 24 hours at 35° C. and finally centrifuged. The solid residue is dried at room temperature under a stream of nitrogen. The resulting dry product is characterized by means of an X-ray diffraction diagram as crystal modification F of dicyclanil.

EXAMPLE 8
Production of Crystal Modification G

In 6.2 g water 605 mg dicyclanil of crystal modification A are suspended and stirred at 80° C. for 16 hours. After filtration and drying at 22° C. for 7 hours the X-ray diffraction diagram characterizes the product as crystal modification G with a water content of less than 0.5%, measured by means of thermogravimetry.

What is claimed is:

1. Crystal modification D of a compound of formula I

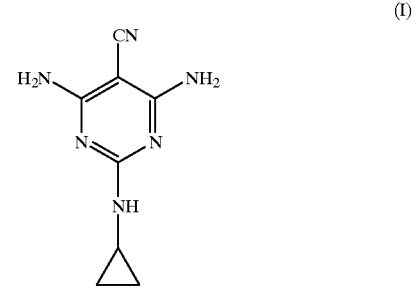

(I)

in substantially pure form, which, when measured in DSC, exhibits a transformation in a temperature range of between 150° C. and 166° C. at a heating rate of 10° C./min., and possesses the following characteristic interlattice plane distances (in [Å]) from X-ray diffraction measurements: 11.4±0.2, 8.7±0.2, 7.1±0.2, 5.92±0.05, 5.75±0.05, 5.70±0.05, 4.45±0.05, 4.40±0.05, 4.15±0.05, 3.96±0.05, 3.94±0.05, 3.80±0.05, 3.78±0.05, 3.72±0.05, 3.53±0.05, 3.41±0.05, 3.32±0.05, 2.96±0.05, 2.92±0.05, 2.84±0.05 and 2.83±0.05.

2. A process for the production of the crystal modification D of the compound of formula I according to claim 1, wherein a suspension of the compound of formula I of known or unknown or unspecified morphological composition with a grain size distribution of 0.4 to 6 μm is maintained at elevated temperature in a solvent or in a mixture of solvents.

3. Process according to claim 2 wherein the solvent comprises low alcohols or mixtures thereof with water.

4. Process according to claim 3 wherein the solvent comprises 1-octanol and 1,2-propanediol or mixtures thereof with water.

5. Process according to claim 3 wherein the solvent comprises 1-octanol.

6. Process according to claim 2 wherein a temperature range from about room temperature to the boiling point of the solvent or solvent mixture is maintained.

7. Process according to claim 6 wherein a temperature range from about 30° C. to 60° C. is maintained.

8. Process according to claim 7 wherein a temperature range from about 35° C. to 50° C. is maintained.

9. The process according to claim 2 wherein at least one seeding crystal of the crystal modification D of the compound formula I according to claim 1 is added to the suspension.

10. The process according to claim 2 wherein a known crystal modification of the compound of formula I according to claim 1 is suspended in 1-octanol, optionally a seeding crystal of the crystal modification D of formula I according to claim 1 is added, a temperature of about 50.0° C. is maintained in a water bath, and stirring is effected for about 24 hours at this temperature.

11. A composition comprising the crystal modification D of the compound of formula I according to claim 1 and a suitable veterinary carrier.

12. A process for the control of ectoparasites or insect pests comprising contacting the ectoparasite or insect pest with an effective amount of the composition according to claim 11.

13. The crystal modification D of the compound of formula I according to claim 1 as a dihydrate containing the following characteristic interlattice plane distances (in [Å]) from X-ray diffraction measurements: 8.9, 8.4, 6.8, 6.3, 4.41, 4.32, 3.97, 3.70, 3.57, 3.48, 3.43, 3.35, 3.19, 3.17, 3.02, 3.01, 2.92, 2.87, 2.70, 2.66, 2.64, 2.48, 2.34, 2.32, 2.23, 2.16, 2.14, 2.02, 1.88, 1.85.

14. The crystal modification D of the compound of formula I according to claim 1 containing the following characteristic interlattice plane distances (in [Å]) from X-ray diffraction measurements: 9.2, 8.3, 5.89, 4.59, 4.41, 3.68, 3.36, 3.11, 3.06, 3.00, 2.97, 2.92, 2.82, 2.68, 2.64.

15. The crystal modification D of the compound of formula I according to claim 1 containing the following characteristic interlattice plane distances (in [Å]) from X-ray diffraction measurements: 11.3, 9.3, 9.1, 8.6, 8.4, 7.9, 6.9, 6.4, 5.91, 5.67, 4.48, 4.37, 4.10, 3.99, 3.86, 3.77, 3.52, 3.49, 3.31, 3.25, 3.17, 3.11, 3.04, 2.96, 2.90, 2.87, 2.83, 2.66, 2.63.

16. The crystal modification of the compound of formula I according to claim 1 containing the following characteristic interlattice plane distances (in [Å]) from X-ray diffraction measurements: 9.0, 8.3, 7.8, 5.92, 5.59, 5.37, 4.94, 4.60, 4.52, 4.43, 4.14, 3.98, 3.84, 3.81, 3.68, 3.63, 3.33, 3.08, 3.07, 3.01, 2.97, 2.94, 2.83, 2.69.

17. The process according to claim 12 wherein an effective amount of the composition is applied to domestic or farm animals to protect them from ectoparasites or insect pests.

18. The process according to claim 17 wherein the ectoparasites or insect pests are of the Diptera species.

19. The process according to claim 17 wherein the composition is applied to domestic or farm animals by a pour on or drench process.

* * * * *